United States Patent [19]

Fusco

[11] 4,120,789

[45] Oct. 17, 1978

[54] METHOD FOR THE PURIFICATION OF SEWAGE WATERS WHICH CONTAIN ORGANIC COMPOUNDS OF AN ANIONIC NATURE

[75] Inventor: Raffaele Fusco, Milan, Italy

[73] Assignee: ANIC, S.p.A., Palermo, Italy

[21] Appl. No.: 768,837

[22] Filed: Feb. 15, 1977

[30] Foreign Application Priority Data

Feb. 23, 1976 [IT] Italy ............................... 20456 A/76

[51] Int. Cl.$^2$ ............................ C02B 1/20; C02C 5/02
[52] U.S. Cl. ..................................................... 210/54
[58] Field of Search ....................... 210/54, 47, 51–53

[56] References Cited

U.S. PATENT DOCUMENTS

| | | | |
|---|---|---|---|
| 3,617,570 | 11/1971 | Redmore | 210/54 |
| 3,880,753 | 4/1975 | Panzer et al. | 210/54 |
| 3,962,332 | 6/1976 | Trapasso | 210/54 |
| 4,000,069 | 12/1976 | Fusco | 210/54 |

*Primary Examiner*—Thomas G. Wyse
*Attorney, Agent, or Firm*—Ralph M. Watson

[57] ABSTRACT

Bis-guanylhydrazonium and tris-guanylhydrazonium salts are disclosed, which are novel and very effective precipitants of anionic pollutants from sewage waters. Methods of preparation of such compounds and examples of their practical use are also reported.

5 Claims, No Drawings

METHOD FOR THE PURIFICATION OF SEWAGE WATERS WHICH CONTAIN ORGANIC COMPOUNDS OF AN ANIONIC NATURE

This invention relates to a method for the purification of sewage waters which contain organic compounds of an anionic nature, said method exploiting the use of salts of bis-guanylhydrazonium and tris-guanylhydrazonium.

It is known that many organic compounds having an anionic nature can be found in the industrial sewage waters and that often their elimination is both very difficult and expensive.

It has now been surprisingly found, and this is the subject of the present invention, that certain classes of such anionic compounds can be precipitated, quantitatively or nearly so, by employing bis-guanylhydrazonium- and tris-guanylhydrazonium salts: these salts form, with said anionic compounds, saline derivatives which are very poorly water-soluble so that they can easily be removed.

More particularly, a number of classes of dyestuffs, having in their molecules one or more sulphonic groups, can be precipitated with the novel reagents the subject of the present invention.

This property can be exploited to remove the dyestuffs from the residue of a dye bath, especially when the dye-stuffs cannot be abated with the usual inorganic precipitants (such as calcium hydroxide and aluminum sulphate).

Even in the cases where the usual precipitants are effective, it has been found that to match these with the novel compounds affords advantages, both to the end of a more complete purification and because the bulk of the sludges can considerably be reduced thereby, their disposal being thus greatly facilitated.

Another interesting property of the novel products of the present invention is that they provide saline compounds which are highly insoluble with many anionic capillary-active substances which are available on the market, such as alkylbenzenesulphonic acid esters, both with straight and branched chain and the acidic alkyl sulphates having a long-chained structure.

Such an important property can be exploited to remove in an insoluble form the residues of like capillary-active substances which are contained in the sewage waters of numerous industries and which are notoriously difficult to strip by biological degradation or otherwise.

It is quite obvious that the purification of sewage waters containing simultaneously dyestuffs and capillary-active substances of the kind referred to above, such as the sewage waters of dyeing installations, can efficiently be achieved with the products according to the present invention, with the additional advantage that other bodies which are present in dispersed form, such as the dispersed dyestuffs which are incorporated in the precipitate, can concurrently be removed.

The compounds according to the present invention are water-soluble compounds, having a neutral reaction and which are nontoxic for humans and animals in general, non-corrosive and devoid of any odor, so that the possible presence of traces of such compounds in the clear waters after the depollutant treatment cannot cause any damage to the fish fauna or display any unpleasant or detrimental effect.

The novel compounds which are encompassed by the scope of the present invention comprise the salts of bis-guanylhydrazonium and of tris-guanylhydrazonium dicarbonyl or tricarbonyl compounds, respectively.

The former salts can be represented by the general formula:

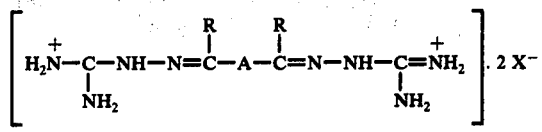

wherein:

R can be a hydrogen atom or a lower aliphatic chain ($C_1$ to $C_3$); A represents aromatic rings connected through heteroatoms to other aromatic rings or to aliphatic chains; $X^-$ is an inorganic or organic anion such as $Cl^-$, $Br^-$, $OSO_4H^-$, $NO_3^-$, $CH_3SO_3^-$, $Ar-SO_3^-$, and others.

By way of example but without any limitation, A can be:

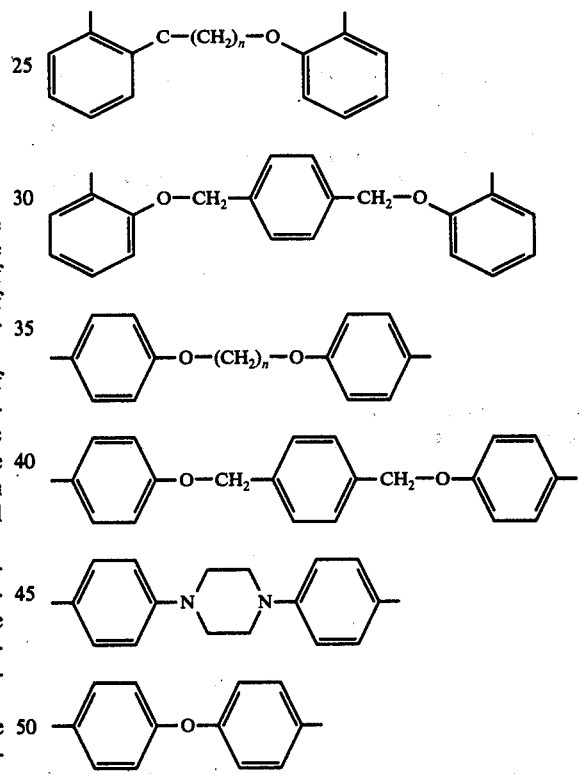

These compounds can be prepared by reacting a salt of aminoguanidine with dicarbonyl compounds of the structure:

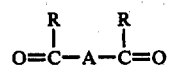

wherein A and R have the meanings indicated hereinabove.

The reaction between the two components can take place in a solvent such as water or in watermiscible solvents (such as ethanol, methanol, etc.), during a time sufficient to complete the reaction at a temperature ranging from room temperature and the boiling point temperature of the solvent concerned.

The selection of the solvent will be directed from time to time by criteria of opportunity such as the cost and the possibility of an easy recovery, the reaction affinity of the components of the solvent and the reaction time.

The salts of tris-guanylhydrazonium, in their turn, can be represented by the general formula:

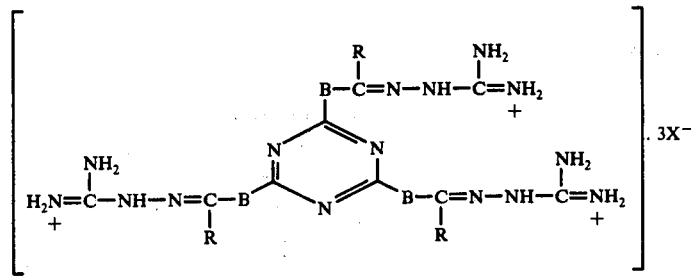

wherein:
R can be a hydrogen atom or a lower aliphatic chain ($C_1$–$C_3$), B is an aromatic ring bound by oxygen atoms to the triazine system, $X^-$ has the same meaning as reported hereinabove.

By way of example and without limitation B can be:

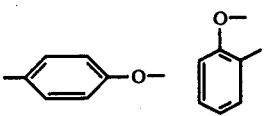

These compounds can be prepared by reacting a salt of aminoguanidine with tricarbonyl compounds of the pattern:

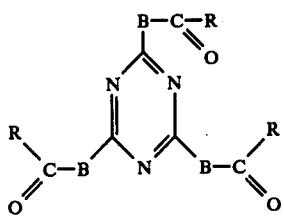

wherein B and R have the meanings indicated above.

The mode of reaction is quite similar to that which has been indicated for the bis-guanylhydrazonium salts.

EXAMPLE 1

Bis-guanylhydrazonium salt from aminoguanadine bicarbonate and
2,2'-(hexamethylene-bis-oxy)-dibenzaldehyde 13.6 grams of aminoguanidine bicarbonate are treated with 17 mls of 18%-HCl.

Then are added 16.3 grams of 2,2'-(hexamethylene-bis-oxy)-dibenzaldehyde slurried in 100 mls of absolute methanol.

Heat to 90° C. during two hours. The solution is concentrated and upon cooling the salt of bis-guanylhydrazonium is obtained.

Yield 87%, melting point 220° C.–221° C.

EXAMPLE 2

Bis-guanylhydrazonium salt from aminoguanidine bicarbonate and
2,2'-(p-phenylene-bis-methyloxy)-dibenzaldehyde 1.41 grams of amionguanidine bicarbonate are treated with 2 mls of 18%-HCl.

There are added then 1.8 grams of 2,2'-(p-phenylene-bis-methylenoxy)-dibenzaldehyde slurried in 30 mls. of absolute methanol. The mixture is heated to 90° C. during 2½ hours. The solution is concentrated and upon cooling the salt of bis-guanylhydrazonium is obtained.

Yield 89%. Melting point 246° C.–248° C.

EXAMPLE 3

Bis-guanylhydrazonium salt from aminoguanidine bicarbonate and
4,4'-(decamethylene-bis-oxy)-diacetophenone 1.92 grams of aminoguanidine bicarbonate are treated with 2.6 mls of 18%-HCl. There are added now 2.9 grams of 4,4'-(decamethylene-bis-oxy)-diacetophenone slurried in 40 mls of absolute methanol. The reaction mixture is heated to 90° C. during 2½ hours. The solution is concentrated and upon cooling the salt of bis-guanylhydrazonium is obtained.

Yield 74%. Melting point 136° C.–138° C.

EXAMPLE 4

Bis-guanylhydrazonium salt from aminoguanidine bicarbonate and
2,2'-(hexamethylene-bis-oxy)-diacetophenone 2.2 grams of aminoguanidine bicarbonate are treated with 2.9 mls of 18%-HCl. There are added then 2.83 grams of 2,2'-(hexamethylene-bis-oxy)-diacetophenone slurried in 40 mls of absolute methanol. The mixture is heated to 90° C. during 2½ hours. The solution is concentrated and the bis-guanylhydrazonium salt is obtained; it has a rubbery consistency. Yield 82%.

EXAMPLE 5

Bis-guanylhydrazonium salt from aminoguanidine bicarbonate and
4,4'-(p-phenylene-bis-methylenoxy)-dibenzaldehyde 11.6 grams of aminoguanidine bicarbonate are treated with 14 mls of 18%-HCl. Then, there are added 14.5 grams of 4,4'-(p-phenylene-bis-methylenoxy)-dibenzaldehyde slurried in 150 mls of absolute methanol. The mixture is then heated to 90° C. during 2 hours. Upon cooling the solution and recovering the salt of bis-guanylhydrazonium, a yield of 88% is obtained. Melting point 299° C.–301° C. (dec.).

EXAMPLE 6

Bis-guanylhydrazonium salt from aminoguanidine bicarbonate and 4,4'-diacetyl-diphenylether 13.6 grams of aminoguanidine bicarbonate are treated with 17 mls. of 18%-HCl. There are then added 12.7 grams of 4,4'-diacetyl-diphenyl-ether slurried in 100 mls of absolute methanol. The mixture is heated to 90° C. during 2 hours. The solution is concentrated and the salt of bis-guanylhydrazonium is obtained upon cooling the solution.

Yield 96%. Melting point 217° C.–219° C.

EXAMPLE 7

Bis-guanylhydrazonium salt from aminoguanidine bicarbonate and N,N'-(p-formylphenyl)-piperazine 2.72 grams of aminoguanidine bicarbonate are treated with 3.5 mls of 18%-HCl. There are then added 2.94 grams of N,N'-(p-formylphenyl) piperazine slurried in 50 mls of absolute methanol. The mixture is heated to 90° C. during 2 hours. The solution is cooled and the bis-guanylhydrazonium salt is recovered.

Yield 95%. Melting point 290° C. (dec.).

EXAMPLE 8

Tris-guanylhydrazonium salt from aminoguanidine bicarbonate and 2,4,6-tri-(p-acetylphenoxy)-1,3,5-triazine 1.15 grams of aminoguanidine bicarbonate are treated with 1.5 ml of 18%-HCl. There are then added 2/94 grams of 2,4,6-tri-(p-acetylphenoxy)-1,3,5-triazine slurried in 30 mls of absolute methanol. The mixture is heated at 90° C. during 3 hours. The solution is concentrated until obtaining a solid which is dissolved in a marge volume of ethanol. By adding ethyl acetate, the salt of tris-guanylhydrazonium is precipitated.

Yield 51%. Melting point 250° C. approx., with softening at about 220° C.

EXAMPLE 9

Tris-guanylhydrazonium salt from aminoguanidine bicarbonate and 2,4,6-tri-(o-formylphenoxy)-1,3,5-triazine 2.04 grams of aminoguanidine bicarbonate are treated with 2.72 mls of 18%-HCl. There are then added 2.21 grams of 2,4,6-tri-(o-formylphenoxy)-1,3,5-triazine slurried in 50 mls of absolute methanol. The mixture is heated to 90° C. during 3 hours. The solution is concentrated and cooled, the tris-guanylhydrazonium salt being thus obtained.

Yield 68%. Melting point over 260° C. with softening at 150° C.

EXAMPLE 10

Tris-guanylhydrazonium salt from aminoguanidine bicarbonate and 2,4,6-tri-(p-formylphenoxy)-1,3,5-triazine 2.04 grams of aminoguanidine bicarbonate are treated with 2.72 mls of 18%-HCl. There are then added 2.21 grams of 2,4,6-tri-(p-formylphenoxy)-1,3,5-triazine slurried in 50 mls of absolute methanol. The mixture is heated to 90° C. during 3 hours. Upon cooling, the salt of tris-guanylhydrazonium is precipitated, with ethyl acetate.

Yield 53%. Melting point 250° C.–255° C. (dec.).

EXAMPLE 11

2,2'-(p-phenylene-bis-methylene-oxy)-dibenzaldhyde

To the boiling solution of 2.5 grams of the sodium salt of the salicylaldehyde in 15 mls of dimethylformamide, is added during 10 minutes 1.54 gram of 1,4-bis-chloromethylbenzene in 10 mls of dimethylformamide. The mixture is refluxed during 2 hours. Upon cooling the mixture is poured over 300 mls of iced water and allowed to stand 1 hour. Filtration is carried out, washing with methanol and recrystallization from chloroform is effected, the substituted dibenzaldehyde being thus obtained.

Yield 79%. Melting point 174° C.–176° C.

EXAMPLE 12

4,4'-(p-phenylene-bis-methylene-oxy)-dibenzaldehyde

To a boiling solution of 23 grams of the sodium salt of p-oxybenzaldehyde in 70 mls of dimethylformamide are added during 15 minutes 14 grams of 1,4-bis-chloromethylbenzene in 50 mls of dimethylformamide. The mixture is refluxed during 2 hours. The mixture is then cooled, poured in 2 liters of iced water and allowed to stand for one hour. Upon filtration and washing with methanol, recrystallization from chloroform is carried out and the substituted dibenzaldehyde is obtained.

Yield 84%. Melting point 161° C.–162° C.

EXAMPLE 13

Examples of purification

To standard solutions of dyestuffs (200 milligrams per liter) is added a solution of bis-guanylhydrazonium salt according to Example 1 hereof (10 grams per liter). The as-formed precipitate is allowed to stand and the color of the solution is observed.

The results are reported in the following Table.

| Type of dyestuffs | Weight ratio dyestuff to precipitate | Aspect of the supernatant liquor without dilutions |
|---|---|---|
| Remazol B black | 1-1 | Colorless |
| Lavafix RB blue | 1-1 | Colorless |
| Lavafix H3 BLA dark green | 1-1 | Colorless |
| Remazol G turquois blue | 1-1 | Colorless |
| Procyon 3BS scarlet | 1-1 | Colorless |
| Lavafix E4B red | 1-1 | Colorless |
| Procyon MX 2R orange | 1-1 | Very light color |
| Lavafix EG golden yellow | 1-1 | Colorless |
| Lavafix E3G yellow | 1-1 | Colorless |

EXAMPLE 14

Example of purification

To 2 liters of a solution taken from a dyeing and washing bath of 4,000 liters containing 1.25 kilograms of Procyon MXR2 orange, 1.11 kilograms of Lavafix EG yellow, 0.09 kilograms of Lavafix E4D red, 1 kilogram of a nonionic capillary-active agent, 1 kilogram of sulphonated lauryl alcohol, 80 kilograms of $Na_2SO_4$ and 21 kilograms of $Na_2CO_3$ adjusted to a pH of 7 by $H_2SO_4$, is added a solution of 2 grams of bis-guanylhydrazonium salt as made according to Example 1.

Decantation is allowed to proceed during 30 minutes. A sample of the supernatant liquor diluted with water at 1/20 and looked through a thickness of 10 centimeters was colorless.

EXAMPLE 15

Examples of purification

To 100 mls-samples of the solution of dyeing and washing described in Example 14, adjusted to pH 7, are added solutions of 0.1 grams of salts of bis- and tris-guanylhydrazonium. Decantation is allowed to proceed during 10 minutes.

The results which have been obtained are reported in the following Table:

| Salt of guanylhydrazonium used, as obt. in Example No. | Aspect of the supernatant liquor diluted with water at 1 to 20 |
| --- | --- |
| 2 | Very light color |
| 6 | Very light color |
| 7 | Light color |
| 8 | Very light color |

I claim:

1. The method of purifying sewage water by removing therefrom an anionic organic compound contained therein that reacts with a bis-guanylhydrazonium or tris-guanylhydrazonium salt represented by the formulae:

$$\left( H_2\overset{+}{N}-\underset{NH_2}{\underset{|}{C}}=NH-N=\overset{R}{\overset{|}{C}}-A-\overset{R}{\overset{|}{C}}=N-NH-\underset{NH_2}{\underset{|}{C}}=\overset{+}{N}H_2 \right) \cdot 2X^-$$

or

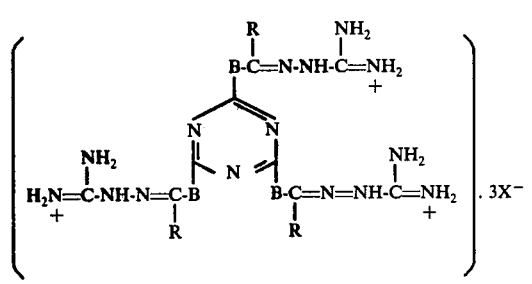

wherein:
R is hydrogen or an aliphatic chain having from 1 to 3 C, atoms,
A represents aromatic rings connected through heteroatoms to other aromatic rings or to aliphatic chains,
B represents an aromatic ring bound by oxygen atoms to the triazine system,
$X^-$ represents an anion consisting of $Cl^-$, $Br^-$, $OSO_4H^-$, $NO_3^-$, $CH_3SO_3^-$ or $Ar-SO_3^-$,
to form a saline derivative that is very poorly water-soluble, which comprises adding to said sewage water an effective quantity of at least one of said bis-guanylhydrazonium or tris-guanylhydrazonium salts so that a precipitate and a supernatant liquor are formed, and then decanting said supernatant liquor.

2. The method of purifying sewage water as claimed in claim 1, wherein said anionic organic compound is a dyestuff having at least one sulphonic group in the molecule.

3. The method of purifying sewage water as claimed in claim 2, wherein said sewage water is the residue of a dye bath.

4. The method of purifying sewage water as claimed in claim 1, wherein A represents a member of the group consisting of:

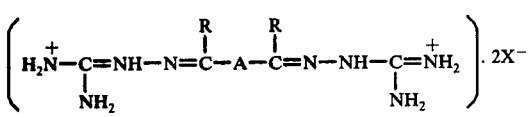

5. The method of purifying sewage water as claimed in claim 1, wherein B is:

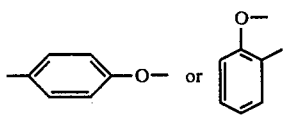

* * * * *